United States Patent [19]

Bretschneider

[11] 4,415,556

[45] Nov. 15, 1983

[54] PROTECTIVE SOLUTION FOR HEART AND KIDNEY AND PROCESS FOR ITS PREPARATION

[75] Inventor: Hans-Jurgen Bretschneider, Bovenden, Fed. Rep. of Germany

[73] Assignee: Dr. Franz Köhler Chemie GmbH, Alsbach-Bergstrasse, Fed. Rep. of Germany

[21] Appl. No.: 329,078

[22] Filed: Dec. 9, 1981

[30] Foreign Application Priority Data

Dec. 23, 1980 [CH] Switzerland .................... 9510/80

[51] Int. Cl.³ .................... A61K 31/19; A61K 31/40; A61K 31/70; A61K 33/06; A61K 33/10; A61K 33/14
[52] U.S. Cl. .................... 424/153; 424/154; 424/156; 424/180; 424/274; 424/317
[58] Field of Search ............... 424/153, 274, 180, 158, 424/156, 317

[56] References Cited

PUBLICATIONS

Chem. Abst. 84-(1976)-99228z.
Chem. Abst. 93-(1980)-147369f.

Primary Examiner—Stanley J. Friedman
Attorney, Agent, or Firm—Toren, McGeady and Stanger

[57] ABSTRACT

The invention relates to an improved protective solution for preventing ischemia damage to the heart and kidneys, and other organs during operations and transplantations, characterized by the fact that it contains α-ketoglutarate and a buffer system based on histidine/histidine hydrochloride and tryptophane, as well as the usual electrolytes for cardioplegic solutions.

The invention also relates to a process for the preparation of such a protective solution.

5 Claims, No Drawings

PROTECTIVE SOLUTION FOR HEART AND KIDNEY AND PROCESS FOR ITS PREPARATION

BACKGROUND OF THE INVENTION

1. Field of the Invention

The present invention relates to an improved solution to protect the heart, kidney and other organs from being damaged by blood circulation stoppage during operations and transplant as well as to a process for the preparation of such a solution.

2. Description of the Prior Art

New surgical procedures for reconstructing serious congenital deformations of the heart, improvements in cardiac valve protheses and advances in the surgery of coronary vessels have opened up the possibility of completely restoring the health of the most seriously ill. While the heart-lung machine technique only minimally hinders the results of complicated heart operations, the ischemia tolerance, i.e., the tolerance of the organ to a complete interruption of its blood and oxygen supply by disconnecting it from the total circulation, is still an important limiting factor.

After completely interrupting the blood and oxygen supply, the energy balance and the functional capacity of the heart are disturbed rapidly. For this reason, the method of separately supplying the coronary vessels more or less continuously with blood by means of special pumps and cannulae is practiced by some heart surgeons. This coronary perfusion technique is however also associated with serious disadvantages. Namely, the main branches of the coronary vessels cannot always be cannulated completely, the coronary catheters and the organ, supplied with blood, hinder the field of the operation, and the beating heart makes the use of microsurgical methods with the surgical microscope impossible.

For this reason, the technique of artificially stopping the heart with total interruption of the blood supply was developed. The ischemic stopped heart survives for 20 to 40 minutes, depending on previous damage and on the temperature. The exhaustion of energy reserves, which arises in such a procedure, frequently makes a prolonged period of recovery necessary, with use of the heart-lung machine to relieve the stress on the heart, and necessitates an intensive supervision of the more endangered patients in the first postoperative days. In addition, because of the different and complicated surgical interventions, the surgeon is under a considerable time pressure because he must avoid exceeding the very limited ischemia tolerance time under all circumstances.

The limited duration of the operation in the purely ischemic cardiac standstill was the inducement for numerous attempts to improve the protection of the myocardium, for example, through acetylcholine, through magnesium salts, through novocaine, and through the sodium-deficient, calcium-free, novocaine-containing cardioplegic solution, described by H. J. Bretschneider in 1964 (H. J. Bretschneider: Survival and Resuscitation Times of the Heart in the Case of Normothermy and Hypothermy; Verh. Dtsch. Ges. Kreislaufforschg., 30 (1964), 11; H. J. Bretschneider, G. Hubner, D. Knoll, B. Lohr, H. Nordbeck and P. G. Spieckermann: Myocardial Resistance and Tolerance to Ischemia: Physiological and Biochemical Basis; J. of Cardiovasc. Surg., 16 (1975) 241). This cardioplegic solution guarantees an ischemia tolerance time which is approximately twice that of the purely ischemic cardiac standstill. Nevertheless, because of the great advances in surgical techniques, it has become urgent that the duration of ischemia, which is well tolerated by the heart, be lengthened even further and extended to 100 to 120 minutes at 30° C. At the same time, the recovery time necessary must remain as short as possible; only about 10 minutes, in order to keep the total length of time, during which the heart-lung machine is used, as short as possible.

In European patent application No. 12272, a protective solution for the heart, kidneys and other organs is described which is characterized by a buffer system based on histidine, histidine hydrochloride, and tryptophane and which additionally contains sodium, potassium and magnesium ions as well as a polyol or a sugar. With such a protective solution, an ischemia tolerance time having an improvement factor of 4-8 relative to the unaffected heart can be attained.

SUMMARY OF THE INVENTION

I have discovered that the quantitative degree of performance of the protective solution, described in the above mentioned patent application, can be increased significantly by the addition of α-ketoglutarate. By such an addition, it is possible to do without the addition of lithium ions and the previously high concentrations of the histidine/histidine hydrochloride buffer can be partially replaced by the α-ketoglutarate.

I have further discovered a method for preparing the composition of the present invention comprising the steps of dissolving α-ketoglutarate in water along with the histidine, histidine hydrochloride and conventional electrolytes while maintaining the osmolarity of the solution in the range from about 300 to 350 mosm and the pH in the range from about 6.8 to 7.4.

DESCRIPTION OF THE PREFERRED EMBODIMENT

The addition of α-ketoglutarate to the organ-protective solution improves the aerobic metabolism during the approximately 10 minutes-long perfusion of the organ with the protective solution. This improvement in the aerobiosis proceeds without an increase in the basic metabolism. It is probably partly based on a suppression of unfavorable lipolytic processes as well as on an inhibition of undesirable lipolytic transamination processes. Through the inclusion of the α-ketoglutarate in the citrate cycle, NADH (nicotinyl-adenine-dehydrogenase) is relatively economized and, in so doing, a particularly advantageous starting situation is created for the following ischemia time.

The protective solution of the present invention for preventing ischemia damage to the heart and kidneys and other organs, such as, the liver, muscle, and central nervous system during operations or while transplanting these organs is therefore characterized by the fact that it contains α-ketoglutarate and a buffer system composed of histidine, histidine hydrochloride, and tryptophane, as well as the usual electrolytes for cardioplegic solutions. Typical of such electrolytes are sodium chloride, potassium chloride, and magnesium chloride. In addition, a polyol or a sugar is added.

The α-ketoglutaric acid is preferably in the form of its acid alkali salts, for example, in the form of potassium hydrogen α-ketoglutarate, or sodium hydrogen α-ketoglutarate. In determining the composition of the remaining components of the solution, the potassium or sodium content is appropriately taken into consideration.

The quantitative composition of the inventive protective solutions adheres approximately to the following limits:

| | | |
|---|---|---|
| Potassium or sodium hydrogen α-ketoglutarate | 4 ± | 3 millimoles |
| Sodium chloride | 15 ± | 8 millimoles |
| Potassium chloride | 10 ± | 8 millimoles |
| Magnesium chloride | 10 ± | 2 millimoles |
| Tryptophane | 2 ± | 1 millimole |
| Histidine | 150 ± | 100 millimoles |
| Histidine hydrochloride | 16 ± | 11 millimoles |
| Mannitol | 50 ± | 50 millimoles and/or |
| Fructose | 50 ± | 50 millimoles and/or |
| Ribose | 50 ± | 50 millimoles and/or |
| Inosine | 50 ± | 50 millimoles |
| per liter of water. | | |

The osmolarity of the protective solutions should be between 300 and 500 mosm and the pH between about 6.8 and 7.4.

The process for the preparation of a solution for preventing ischemia damage to the heart and kidneys and other organs during operations and while transplating these organs dissolving the following components in water. (Amounts are per 1 liter of water.)

| | |
|---|---|
| 4 ± 3 | millimoles of potassium or sodium hydrogen α-ketoglutarate |
| 15 ± 8 | millimoles of sodium chloride |
| 10 ± 8 | millimoles of potassium chloride |
| 10 ± 2 | millimoles of magnesium chloride |
| 2 ± 1 | millimole of tryptophane |
| 150 ± 100 | millimoles of histidine |
| 16 ± 11 | millimoles of histidine hydrochloride |

At least one polyol or at least one sugar is added, and maintaining the osmolarity of the solution at about 300 to 350 mosm and adjusting the pH of the solution to 6.8 and 7.4.

EXAMPLE 1

Protective solution for heart, kidneys and other transplantable organs

The following are dissolved in 1 liter of freshly distilled water:

| | | |
|---|---|---|
| potassium hydrogen α-ketoglutarate | 4 mmoles = | 8 mosm |
| sodium chloride | 15 mmoles = | 30 mosm |
| potassium chloride | 10 mmoles = | 20 mosm |
| magnesium chloride | 10 mmoles = | 30 mosm |
| histidine | 150 mmoles = | 150 mosm |
| histidine hydrochloride | 16 mmoles = | 32 mosm |
| tryptophane | 2 mmoles = | 2 mosm |
| mannitol | 50 mmoles = | 50 mosm |
| Osmolarity | | 322 mosm |

EXAMPLE 2

Protective solution for heart and kidneys

The following are dissolved in 1 liter of freshly distilled water:

| | | |
|---|---|---|
| sodium hydrogen α-ketoglutarate | 1 mmole = | 2 mosm |
| sodium chloride | 15 mmoles = | 30 mosm |
| magnesium chloride | 10 mmoles = | 30 mosm |
| tryptophane | 2 mmoles = | 2 mosm |
| histidine | 150 mmoles = | 150 mosm |
| histidine hydrochloride | 16 mmoles = | 16 mosm |
| fructose | 50 mmoles = | 50 mosm |
| mannitol | 50 mmoles = | 50 mosm |
| Osmolarity | | 330 mosm |

EXAMPLE 3

Protective solution for heart and kidneys

The following are dissolved in 1 liter of freshly distilled water:

| | | |
|---|---|---|
| potassium hydrogen α-ketoglutarate | 6 mmoles = | 12 mosm |
| sodium chloride | 15 mmoles = | 30 mosm |
| potassium chloride | 10 mmoles = | 20 mosm |
| magnesium chloride | 12 mmoles = | 36 mosm |
| tryptophane | 2 mmoles = | 2 mosm |
| histidine | 50 mmoles = | 50 mosm |
| histidine hydrochloride | 5 mmoles = | 5 mosm |
| ribose | 75 mmoles = | 75 mosm |
| inosine | 75 mmoles = | 75 mosm |
| Osmolarity | | 305 mosm |

The progress of the inventive protective solution over the state of the art is proven by the following comparison with previously known cardioplegic solutions.

Cardioplegic Comparison Solution

1./2. The cardioplegic solution 1, was described in 1964 (H. J. Bretschneider, Survival and Resuscitation Times of the Heart in the Case of Normothermy and Hypothermy; Verh. Dtsch. Ges. Kreislaufforschung. 30. (1964), 11) and solution 2, which was modified slightly in 1967. These characterize the state of the art somewhat earlier than the present invention.

The following are contained in 1 liter of freshly distilled water:

| | Solution No. 1 | Solution No. 2 |
|---|---|---|
| sodium chloride | 5 mmoles | 12 mmoles |
| potassium chloride | 5 mmoles | 7 mmoles |
| magnesium chloride | — | 1 mmoles |
| glucose | 5.5 mmoles | 11 mmoles |
| procaine | 8.5 mmoles | 8.5 mmoles |
| mannitol | 267.5 mmoles | 241 mmoles |
| osmolarity | 310 mosm | 310 mosm |
| pH | 7.4 | 7.4 |

3. The comparison solution, described in European patent application No. 12272 is characteristic of the most recent prior art and has the following composition:

The following are dissolved in 1 liter of freshly distilled water.

| | | |
|---|---|---|
| sodium chloride | 15 mmoles = | 30 mosm |
| potassium chloride | 10 mmoles = | 20 mosm |
| lithium chloride | 1 mmole = | 2 mosm |
| magnesium chloride | 1 mmole = | 3 mosm |
| histidine | 160 mmoles = | 160 mosm |
| histidine hydrochloride | 16 mmoles = | 32 mosm |
| tryptophane | 2 mmoles = | 2 mosm |
| mannitol | = | 50 mosm |
| | | 299 mosm |

-continued

| pH | = 7.1 |
|---|---|

The ischemia times for solutions No. 1, 2, and 3, and with the inventive solution of Example 2 were determined on dog hearts. The results are set forth in Table 1.

TABLE 1

| Cardioplegic solution | Ischemia times in minutes | | | |
|---|---|---|---|---|
| | at 35° C. | at 25° C. | at 15° C. | at 5° C. |
| No. 1 | 70 | 110 | 256 | 415 |
| No. 2 | 62 | 142 | 282 | 435 |
| No. 3 "HTP" | 100 | 210 | 420 | 800 |
| "HTK" Inventive solution, Example 2 | 120 | 260 | 520 | 1000 |

Pre-ischemic equilibration of the heart with the histidine-tryptophane-polyol solution No. 3 ("HTP" solution) is able to lengthen by a factor of about 8, the ischemia tolerance of the organ in dog experiments, compared to a purely ischemic cardiac standstill at the same temperature (BRETSCHNEIDER, H. J.: Thorac. Cardiovasc. Surgeon 28, 295 (1980)). According to biochemical analyses of 8 dog hearts, the addition of 1 mmole liter of potassium α-ketoglutarate ("HTK" solution) produces an energetic and metabolic improvement in the protection during ischemia in normothermy and hypothermy as is evident from Table 1.

From Table 1, it is clear that the cardioplegic solution, improved by the addition of α-ketoglutarate, is able to lengthen the ischemia tolerance times at 35° C. by ca. 20%, at 25° C. by ca. 20%, at 15° C. by ca. 25%, and at 5° C. by ca. 25%. The fact that the protectively treated heart can be functionally resuscitated very well with the inventively described solution is confirmed by the significant improvement in the biochemical results. The usable ischemia times are measured quantitatively, by measuring the time spans during which the normal ATP content of the miocardium measured at the start of the ischemia does not fall from about 6.5 μmoles/g to the value of 4.0 μmoles/g of heart (moist weight) which is critical and limiting for the resuscitation.

In each of 5 resuscitation experiments—300 minutes of ischemia at an average temperature of 23° C. and subsequent reperfusion and resuscitation with physiological saline Tyrode's solution—a comparison of protective solution No. 3 with that of Example 2 showed a significantly better energy status and therefore a better recovery of the hearts protected with "HTK" (p=0.05; U test of Wilcoxon, Mann and Whitney). The results are shown in Table 2.

TABLE 2

| Metabolites in the myocardium after resuscitation ($\mu$Mol/g; x + S$_x$) | "HTP" Solution Histidine-tryptophane-polyol Solution No. 3 | "HTK" Solution Histidine-tryptophane-α-ketoglutarate Solution according to Example 2 |
|---|---|---|
| ATP content | 4.1 ∓ 0.6 | 4.8 ∓ 0.4 |
| Sum of adenine nucleotides | 5.1 ∓ 0.6 | 5.9 ∓ 0.5 |

The hearts protected with α-ketoglutarate also had a clearly more stable rhythm and were less susceptible to edema during the reperfusion.

According to these findings, the addition of 1 millimole/liter of potassium hydrogen α-ketoglutarate to the cardioplegic solution acts to provide both a clear improvement in the post-ischemic metabolic energetic recovery and a specific structure protection for the ischemic organ.

The general validity of this evidence is supported by 5 experiments on dogs to test the functional reversibility of a renal ischemia of 100 to 120 minutes at an average temperature of 34° C. In each case, the dogs were nephrectomized unilaterally, the remaining kidney equilibrated with the solution of "HTK" and, after the ischemia stress mentioned, "resuscitated" by releasing once again, the perfusion of blood. On the fifth postoperative day, the animals already showed an almost normal creatinine serum value of less than 2 mg percent; similar successes were not achievable without the addition of α-ketoglutarate.

I claim:

1. In a method for preventing ischemia damage to the heart, kidneys and other organs during operations and transplants thereof, wherein an ischemia damage preventing effective amount of a solution containing a buffer system composed of histidine; histidine chloride, and tryptophane and the conventional electrolytes for cardioplegic solutions is administered, the improvement which comprises said solution also containing an ischemia damage protecting amount of α-ketoglutarate.

2. The method of claim 1 wherein the solution further contains potassium and magnesium ions as electrolytes and a polyol or a sugar.

3. A process for the preparation of a solution for preventing ischemia damage to the heart and kidneys during operations and while transplanting the organs, comprising adding to water on a per liter basis:

| 4 ± | 3 millimoles potassium or sodium hydrogen α-ketoglutarate |
|---|---|
| 15 ± | 8 millimoles of sodium chloride |
| 10 ± | 8 millimoles of potassium chloride |
| 10 ± | 2 millimoles of magnesium chloride |
| 2 ± | 1 millimole of tryptophane |
| 150 ± | 100 millimoles of histidine |
| 16 ± | 11 millimoles of histidine hydrochloride; | at least one polyol or sugar, and wherein the osmolarity of the solution is maintained at about 300 to 350 mosm and the pH of the solution is adjusted to 6.8 to 7.4.

4. In a method for preventing ischemia damage to the heart, kidneys and other organs during operations and transplants thereof, wherein an ischemia damage preventing effective amount of a solution is administered by perfusion, the improvement which comprises the solution having the following composition on a per liter basis:

| potassium or sodium hydrogen α-ketoglutarate | 4 ± | 3 millimoles |
|---|---|---|
| sodium chloride | 15 ± | 8 millimoles |
| potassium chloride | 10 ± | 8 millimoles |
| magnesium chloride | 10 ± | 2 millimoles |
| tryptophane | 2 ± | 1 millimole |
| histidine | 150 ± | 100 millimoles |
| histidine hydrochloride | 16 ± | 11 millimoles |
| mannitol | 50 ± | 50 millimoles |
| fructose | 50 ± | 50 millimoles |
| ribose | 50 ± | 50 millimoles |
| inosine | 50 ± | 50 millimoles | the osmolarity of the solution being about 300 to 350 mosm and the pH of the solution lying between 6.8 and 7.4.

5. In a protective solution for preventing ischemia damage to the heart and kidneys in operations and during organ transplants containing a buffer system composed of histidine, histidine hydrochloride, and tryptophane and the conventional electrolytes for cardioplegic solutions, the improvement which comprises said solution having the following composition on a per liter basis

| | | |
|---|---|---|
| potassium or sodium hydrogen α-ketoglutarate | 4 ± | 3 millimoles |
| sodium chloride | 15 ± | 8 millimoles |
| potassium chloride | 10 ± | 8 millimoles |
| magnesium chloride | 10 ± | 2 millimoles |
| tryptophane | 2 ± | 1 millimole |
| histidine | 150 ± | 100 millimoles |
| histidine hydrochloride | 16 ± | 11 millimoles |
| mannitol | 50 ± | 50 millimoles |
| fructose | 50 ± | 50 millimoles |
| ribose | 50 ± | 50 millimoles |
| inosine | 50 ± | 50 millimoles | the osmolarity of the solution being about 330 to 350 mosm and the pH of the solution lying between 6.8 and 7.4.

* * * * *